United States Patent [19]

Gutnick et al.

[11] 3,941,692

[45] Mar. 2, 1976

[54] CLEANING OF CARGO COMPARTMENTS

[76] Inventors: David Gutnick, 60 Tagore St., Tel Aviv; Eugene Rosenberg, 9 Habrosh St., Raanana, both of Israel

[22] Filed: Jan. 10, 1975

[21] Appl. No.: 540,176

Related U.S. Application Data

[63] Continuation of Ser. No. 364,048, May 25, 1973, abandoned.

[30] Foreign Application Priority Data

Apr. 3, 1973 Israel.................................... 41941

[52] U.S. Cl.................................. 210/11; 195/3 H
[51] Int. Cl.².......................................... C02B 9/02
[58] Field of Search............ 195/3 H; 210/2, 11, 15

[56] References Cited
UNITED STATES PATENTS

| | | | |
|---|---|---|---|
| 3,152,983 | 10/1964 | Davis et al. | 210/11 |
| 3,268,412 | 8/1966 | Champagnot et al. | 195/3 H |
| 3,510,403 | 5/1970 | Laine et al. | 195/3 H |
| 3,634,227 | 1/1972 | Patterson | 210/11 |
| 3,769,164 | 4/1973 | Azarowicz | 210/11 |

*Primary Examiner*—Thomas G. Wyse
*Attorney, Agent, or Firm*—Johnston, Keil, Thompson & Shurtleff

[57] ABSTRACT

Oil is removed from sea water, for example, in the cleaning of tanks of oil transport ships, by utilizing bacteria or cell-free solutions from such bacteria in a confined space with the addition of a source of nitrogen and a source of phosphorus, under aerated conditions. The resultant microbial fermentation converts the oil to protein-containing by-products making it possible to discharge the contents of the tanks without oil contamination and, if desired, to recover useful by-products.

6 Claims, No Drawings

3,941,692

CLEANING OF CARGO COMPARTMENTS

This is a continuation of application Ser. No. 364,048, filed May 25, 1973, now abandoned.

This invention relates to the cleaning of maritime vessels, and more particularly, to economical and safe methods for cleaning cargo tank compartments of maritime vessesl that carry petroleum hydrocarbon oils.

Petroleum fuels and good water are two of the modern world's most important necessities, with the demand for both continually increasing. One of the most economical methods of transporting liquid petroleum fuels, such as crude oil, fuel oil, heavy diesel oil and lubricating oil, has been by maritime carriers and, unfortunately, this has led to considerable pollution problems on the high seas and on waterways. This pollution problem has been intensified by the development of very large crude carriers, which formerly were in the size class of 20,000–30,000 DWT, and now range up to 326,000 DWT. It is expected that the pollution problem will be further aggravated by the use of even larger carriers, now being built.

While water pollution occurs through accidental oil spills, an equally serious source of pollution is the petroleum fuel that is intentionally discharged by carriers during the washing of the emptied compartment tanks, and also with the ballast water. The cargo compartments contain considerable amounts of residual fuel oil after they have been emptied and they must be cleaned to eliminate a fire hazard. A recent study of three 70,000 DWT carriers by Cities Service Tankers Corporation over a 3-year period indicated that approximately 0.25–0.30% of the oil remained in the emptied cargo tank. Projecting this percentage to a 326,000 DWT carrier, would indicate a residual oil weight of about 1000 tons. The ballast water is taken on by the emptied carrier during its trip back to the originating port terminal, in order to properly immerse the propeller and rudder for controllability, as well as immerse the ships hull to reduce structural stress. Efforts to control this source of pollution have not been completely successful even though international laws relating to the problem are continually being strengthened. For example, regulations of the International Convention for Prevention of Pollution of the Seas by Oil (1954, amended 1962, and 1969) specified (1) that the instantaneous rate of oil discharge should not exceed 10 liters per mile, (2) that the total quantity discharged should not exceed 1/15,000 of the total cargo-carrying capacity, and (3) that the tanker should not be less than 50 miles from the nearest land at the time of discharge. These regulations do not apply, however, if the carrier's compartments have been cleaned and the subsequent discharged ballast water does not produce visible traces of oil on the water surface. At the 1970 NATO meeting in Brussels, international support was given for the eventual termination of all intentional discharge of oil from ships into the oceans. These are strong stringent requirements that are obviously necessary to prevent the continuing pollution buildup. Unfortunately, these regulations are difficult to enforce, and surveillance techniques for detection and identification of discharges are not completely developed.

There are some alternative solutions for eliminating the oily ballast discharge. For example, the carriers could be constructed with sufficient clean ballast space so that the water would not have to be taken into the oily cargo compartments. Obviously, this would be an expensive modification in the carrier design and would reduce the ships carrying capacity. Another suggestion is to have ballast water discharge and treatment facilities at the terminal ports, to receive the oily ballast before loading the fresh cargo. Still another suggestion is to clean the ship at a special cleaning station after the cargo has been discharged. These procedures would entail considerable time delay in port as well as the construction of expensive special port facilities. Thus, it would appear that the elimination of water pollution due to the cleaning of cargo compartments or the discharge of oily ballast, requires expensive and time consuming corrective measures.

There is another problem that has to be considered in the washing of the cargo tanks after the oil has been discharged. Serious explosions may occur during the washing procedure, or later on passage. Earlier investigations had indicated that forced ventilation of the cargo tanks before and during the cleaning would reduce the danger of explosions. Recently, however, explosions have occurred in very large crude carriers even though the atmosphere in the cargo tanks was kept below the lower explosive limit. The washing techniques in very large crude carriers involve the use of high velocity rotating jets of cold, clean, unrecirculated seal water, usually at flow rates of approximately 180 tons per hour at 140 psig. The disintegration of the water jet on the tank walls has been shown to give rise to a cloud of charged water droplets, and it is thought that this electrostatic condition is responsible for the ignition of the explosive atmosphere. Obviously it would be very desirable to reduce these electrostatic hazards. Crude oil, however, is an impure product containing insoluble solids and sludge, and the heavy deposits formed on the tank surfaces necessitate stringent cleaning methods. One possible solution would be to use very low pressure water containing chemical detergents; however, the toxicity of the chemical detergents on marine life would have to be considered. Reports in 1968, after the Torrey Canyon Oil Spill, indicated that the chemical detergent that was used, did more biological damage than the oil itself. Present indications are that the use of chemical detergents would add to the pollution problem, unless the cleaning operation was carried out at a shore facility having regulated disposal procedures.

Thus, it would be very desirable to develop other economical methods of cleaning cargo tanks without concurrently increasing the hazard of explosion or the danger of water pollution. It would also be desirable to develop tank cleaning methods that would facilitate the use of ballast water during the voyage.

It is therefore an object of this invention to provide an economical and safe process for cleaning petroleum maritime carrier cargo tank compartments without the danger of creating explosive electrostatic conditions.

Another object is to provide an economical and safe process for the disposal of oily ballast water from petroleum maritime carrier cargo tank compartments without the danger of exceeding International standards of water pollution.

A further object of this invention is to provide an economical and safe process of carrying out the cleaning of the cargo tank compartments and the use of water ballast, in one operation, without the loss of operating time or the need for expensive shore facilities.

Still a further object of this invention is to provide an economical and safe process of carrying out the cleaning of the cargo tank compartments and the use of water ballast, in one operation, and at the same time, of converting the waste petroleum oil in the cargo tank compartment into useful and valuable protein products.

Other objects include the use of petroleum maritime carrier cargo compartments as economical fermentation vessels for the production of valuable products. These and other objects and advantages of the invention will be apparent upon reference to the following description.

In accordance with the invention, it has been discovered that the residual oil in the cargo tanks, after they have been emptied, can be converted wholly or in part to non-oily products by means of microbial action, so that the subsequent cleaning of the cargo compartment can be carried out with a minimum effort and without the buildup of dangerous electrostatic charges. It is an important feature of the invention that microbial cultures or products of microbial cultures, are used to convert the oil to non-oily products, and that the action take place in the cargo compartment, or alternatively, in a conversion system which utilizes the cargo compartment as part of the system.

Although the action of microbial cultures on petroleum products has been known and studied for many years, the degradation of petroleum by marine microorganisms has been investigated primarily in relationship to their effect on oil slicks which pollute the seas. It has been known that the degradation of oil slicks occurs naturally; however, the process is very slow and is rarely of any immediate value in preventing danger to marine life or pollution of the coastal areas. Once the petroleum has been discharged into the sea, and an oil slick formed, there is little that can be done except to attempt to confine and remove the oil. Such methods of treating the oil discharge problem are costly and rarely successful. It is one of the objects of this invention to provide a simple, economical and safe procedure for preventing water pollution from petroleum discharges.

In one embodiment of the invention, sea water is added to the cargo compartment tank, after it has been emptied of its oil. The sea water is added primarily as a vehicle for the subsequent microbial fermentation process and no attempt is made at this point to wash the compartment. The water is preferably added under low pressure without jet nozzles in order to avoid any impingement on the tank walls and resultant buildup of electrostatic charges. Sea water typically contains about 3% salts with relatively low nitrogen and phosphorus levels and it is an important feature of our invention that additional nitrogen and phosphorus must be added to the water, preferably as $KH_2PO_4$, $K_2HPO_4$, $NH_4Cl$, $(NH_4)_2SO_4$, $NH_3$, $NaNO_3$, urea, and the like. Depending on the culture(s) and process, it may also be desirable to add small amounts of other carbohydrate sources such as glucose, starch and the like, and small amounts of other nitrogen sources such as corn steep liquor, peptone, meat extract, yeast extract, fish solubles, and the like. The mixture of residual oil, nutrients and water is then used without sterilization. A preferred suitable microbial inoculum is then added and the fermentation carried out under aerated conditions. Alternatively, a separable microbial inoculum is not added, and the microbial organisms present in the sea water and the fuel oil allowed to grow in the mixture under aerated conditions. It is important that a suitable microbial inoculum is available so that the fermentation results in a relatively rapid degradation of the oil. The fermentation is carried out under aeration, for a period of approximately 1–6 days, during which time the microbial organisms multiply and the oil present in the mixture degraded. It is an important feature of our invention that the fermentation process is carried out under aerated conditions, and that the aeration be carried out in the cargo compartment or in a recirculating system connected to it. After a suitable period of microbial growth, usually 2–4 days, the oil in the mixture is converted, all or in part, to non-oily products. The fermented mixture is then pumped from the cargo compartment and discharged into the sea, without any evidence of a typical oil slick in the wake of the carrier. The portions of the compartment wall in contact with the fermenting mixture are now relatively clean, without any typical sludge, and with only a small amount of oil which is easily washed off with a low pressure water hose.

Alternatively, the fermented mixture in the cargo compartment is not immediately emptied, and serves as ballast during the return voyage. The fermented mixture-ballast is discharged prior to the end of the voyage, and the compartments given a low pressure water rinse to prepare them for the next load of fuel oil. Combining the tank cleaning and the ballast step into one economical and safe operation is a very desirable feature of the invention.

In another modification of the invention, the microbial cells present in the fermented mixture are harvested by any of the procedures known to the art, as for example, centrifugation, and the clarified supernatant discharged into the sea with the excellent results previously observed, while the harvested microbial cells are recovered as a source of protein and other biochemical products.

We have also discovered that certain cultures secrete factor(s) into the supernatant, which rapidly convert oily mixtures into non-oily mixtures suitable for discharge into the sea. These factor(s) act in the absence of the microbial cells which are separated off. It is therefore a further modification of the invention that the cell-free supernatant, which is obtained after the cells are harvested from the fermented mixture, and which contains the oil-dispersing factor(s), is used to convert residual oil in cargo compartments to non-oily mixtures, wholly or in part. It is also part of the invention that the cell-free supernatant, containing the oil-converting factor(s) in crude or purified form, can be produced in suitable fermentation equipment away from the maritime oil carrier, and then supplied to the tanker as required to carry out the residual oil degradation operation. The use of cell-free supernatants, in crude or purified form, to carry out the conversion of the oil to non-oily products is an important feature of the invention.

It is a further important feature of the invention that the culture(s), or alternatively the cell-free factor(s), that are used to carry out the process are selected so as to give the desired degree of conversion of the petroleum product. For example, while almost all kinds of hydrocarbons are susceptible to microbial degradation, some microbial cultures may degrade a particular type of oil slowly while others may degrade the same oil radidly. Similarly, one species may only be able to partially degrade a particular type of oil while another species, which is unable to attack the original oil, is now able to degrade the partially degraded oil. Further, since oils from different sources, and from different strata of the same source, may vary considerably in composition, it is important to be able to use different microbial cultures or cell-free factors, to convert such oils. Thus, in a modification of our process, we use a series of selected microbial cultures of cell-free solutions of factor(s), to carry out the desired degradation. In still another modification, we use different species of microbial cultures growing together, or alternatively, combined cell-free solutions of factor(s) to accomplish the same purpose.

The following examples are illustrative of the methods and compositions according to the invention. It is to be understood that the invention is not limited to the examples nor to the particular materials, proportions, conditions and procedures set forth therein.

EXAMPLE I a. A nutrient medium was prepared from the following materials:

|  | Grams |
| --- | --- |
| Yeast Extract | 0.005 |
| $(NH_4)_2SO_4$ | 1.000 |
| $K_2HPO_4$ | 0.010 |
| Sea water to 1000 ml. | |

The medium was not sterilized and was dispersed 20 ml per 125 ml Erlenmeyer flask. Unsterilized Iranian crude oil (155 mg) was then added to each flask and the flask incubated at 32°C. on a rotary shaker under conditions of aeration and agitation. After about 7 days, the oil which initially was not soluble in the solution, became dispersed throughout the solution.

b. A nutrient medium was prepared as described above under section (a). The medium was dispensed 20 ml per 125 ml Erlenmeyer flask and sterilized at 121°C. for 20 minutes. Iranian crude oil (155 mg), previously sterilized by passage through a 0.45 μm membrane filter (Millipore Corp.), was then added to each flask. The unsterilized bacterial culture (1 ml), prepared and grown as described under section (a), was used to inoculate the sterilized medium, and the inoculated flask incubated at 32°C. on the rotary shaker under conditions of aeration and agitation. The oil which was initially not soluble in the solution, became dispersed throughout the solution in about 2–4 days. It was now possible to maintain this culture population in a viable condition by transfer to fresh medium in a similar manner at 3 day intervals.

c. Sterile nutrient agar medium, or medium supplemented with sterile crude oil were then used to isolate pure bacterial cultures by streaking the mixed bacterial cultures described in section (b). The pure culture isolates which were obtained in this manner, were maintained in viable condition by periodic transfer on nutrient agar.

d. To determine the extent of oil dispersion in the bacterial culture solution, uniform agitated aliquots of the culture solution were transferred to 14×150 mm test tubes, and after a two minute rest period, a 2 ml aliquot was carefully removed from the center of the solution and transferred to micro-Klett tubes. The solution turbidity was then determined using a Klett-Summerson Colorimeter fitted with a green filter. Sterile uninoculated medium was used to determine the solution lbank. Where oil dispersion had occurred, turbidities of 100 to 1,000 Klett Units (KU) were obtained. The turbidity due to the bacterial cells alone was determined to be very low, in the order of 10 KU for $1\times10^8$ bacterial cells per ml.

e. Oil conversion was determined by extracting a 300 ml sample of the culture solution with 300 ml of benzene, separating off the aqueous phase, and reextracting the aqueous phase with an additional 300 ml of benzene. The combined benzene extracts were then filtered through No. 1 Whatman paper, and the solvent evaporated at 37°C. to constant dry weight.

f. Viable cell counts were determined by plating methods using nutrient agar and incubation at 32°C. for 4 days. Within experimental error, the viable cell count was equal to the total cell count determined with a Petroff-Hauser counting chamber.

EXAMPLE II

A nutrient medium was prepared as described in Example I(a) and dispensed 30 ml per 125 ml Erlenmeyer. The medium was sterilized at 121°C. for 20 minutes, and 150 mg of Iranian crude oil, previously sterilized by membrane filtration, added. The flask was inoculated with 0.1 ml of a 2-day old mixed bacterial culture prepared as described in Example I(b), and the inoculated flask incubated at 32°C. on a rotary shaker under conditions of aeration and agitation. The added oil was visibly dispersed in 2–4 days. The data obtained are shown in Table I.

TABLE I

| Days | Solution pH | Cells/ml | Oil Dispersion Klett Units |
| --- | --- | --- | --- |
| 0 | 7.5 | $6.5\times10^6$ | 10 |
| 1 | 6.8 | $3.5\times10^8$ | 30 |
| 2 | 5.1 | $1.5\times10^8$ | 60 |
| 3 | 5.1 | $9.0\times10^7$ | 250 |
| 4 | 5.1 | $6.0\times10^7$ | 370 |

EXAMPLE III

A nutrient medium was prepared and inoculated as described in Example II, except that the flasks were incubated at 32°C. without shaking under conditions of aeration and agitation. There was no visible evidence of oil dispersion after 4 days, or on continued incubation, and the added oil remained as a separate phase on the surface of the medium.

EXAMPLE IV

A nutrient medium was prepared and inoculated as described in Example II, except that in one series of flasks, the $(NH_4)_2SO_4$ plus the $K_2HPO_4$ were omitted from the medium. The flasks were all incubated at 32°C. on a rotary shaker under conditions of aeration and agitation. After 4 days incubation, the medium containing the $(NH_4)_2SO_4$ plus the $K_2HPO_4$ showed visible dispersion of the added oil and had a Klett value of 350. The medium which did not contain these salts showed no signs of oil dispersion and had a Klett value of 10.

EXAMPLE V

A nutrient medium was prepared as described in Example I(a) except that the yeast extract was omitted, and dispensed 30 ml per 250 ml Erlenmeyer. The medium was sterilized at 121°C. for 20 minutes and 125 mg of Iranian crude oil, previously sterilized by membrane filtration, added. The flask was inoculated with 1 ml of a pure bacterial culture which had been isolated following the procedure described in Example I(c). This bacterial culture was characterized bacteriologically as a member of the genus Arthrobacter and was coded RAG-1 (ATCC 31012). The innoculated flask was then incubated at 32°C. on a rotary shaker under conditions of aeration and agitation. As shown by the data in Table II, the results obtained for culture RAG-1 were similar to the results obtained for the mixed culture, with the added oil visibly dispersed in 3 days.

TABLE II

| Days | Solution pH | Cells/ml. | Oil Dispersion Klett Units |
|---|---|---|---|
| 0 | 7.5 | $6.0 \times 10^6$ | 10 |
| 1 | 6.9 | $5.5 \times 10^7$ | 50 |
| 2 | 5.2 | $8.0 \times 10^7$ | 450 |
| 3 | 5.1 | $2.5 \times 10^7$ | 550 |

EXAMPLE VI

The incubated RAG-1 bacterial culture prepared as described in Example V was centrifuged to remove the bacterial cells. The oil dispersing factor(s) produced by the bacterial cells was found to be in the cell-free supernatant, and when crude oil was added to this cell-free supernatant, the oil was visibly dispersed within 60 minutes.

EXAMPLE VII

The starboard slop tank (Tank A) and the port slop tank (Tank B) of a 120,000 ton oil carrier were carefully cleaned prior to taking on a cargo of Agajari crude oil at Kargh Island in the Persian Gulf. These slop tanks measured about 12 meters × 5 meters × 25 meters (depth). After cleaning, and prior to taking on the oil cargo, Tank A was fitted with an aeration system which consisted of a polyethylene pipe (32 mm diameter) which ran from an air compressor on the deck down into the tank, where it was connected to branched polyethylene sections on the tank bottom. The branched bottom polyethylene sections had a total of 50 air holes (2 mm diameter) drilled in the piping to provide uniform distribution of air. The compressor provided air to this system at the rate of 1–3 cubic meters per minute. Tank B was not fitted with an aeration system.

The tanker discharged its cargo of Agajari crude oil at Eilat in the normal manner, and Tanks A and B were not cleaned. The carrier left Eilat, and about 7 hours later, sea water was added to both tanks. The total volume of liquid in Tank A was 107 cubic meters and that in Tank B 121 cubic meters. Urea (20 kilograms) and $K_2HPO_4$ (1 kilogram) were dissolved in sea water and added to Tank A, and similar amounts to Tank B. Air was then introduced into Tank A at the rate of 1–3 cubic meters per minute. Tank A was then inoculated with a suspension of bacteria containing a total of $1 \times 10^{12}$ bacterial cells prepared according to Example V. The value of bacteria at 0 hour was $10^4$ per ml which comprises both the inoculem and bacteria present in the sea water and residual oil.

The tanks were sampled at the start of the test, and every day thereafter. As indicated by the data in Table III, no increase of bacteria occurred in Tank A during the first day; however, there was an increase of over a thousand fold from the first day to the fourth day, when the bacterial count increased from $10^4$ to over $10^7$ per ml. In contrast, Tank B, which was essentially identical to Tank A except that it was not aerated or inoculated, showed a smaller bacterial increase, from $10^4$ to $10^5$ per ml.

TABLE III

| | | Tank A | | | Tank B | |
|---|---|---|---|---|---|---|
| Days | Solution pH | Cells Per ml | Oil Dispersion Klett Units | Solution pH | Cells per ml. | Oil Dispersion Klett Units |
| 0 | 7.8±.2 | $3 \times 10^4$ | 10 | 7.8±.2 | $9 \times 10^3$ | 20 |
| 1 | 7.8±.2 | $3 \times 10^4$ | 17 | 7.8±.2 | $5 \times 10^3$ | 25 |
| 2 | 7.8±.2 | $2 \times 10^5$ | 15 | 7.8±.2 | $1 \times 10^4$ | 15 |
| 3 | 7.8±.2 | $3 \times 10^6$ | 20 | 7.8±.2 | $3 \times 10^4$ | 35 |
| 4 | 7.8±.2 | $1 \times 10^7$ | 175 | 7.8±.2 | $1 \times 10^5$ | 50 |
| 5 | 7.8±.2 | $2 \times 10^7$ | 300 | 7.8±.2 | $1 \times 10^5$ | 60 |

Oily ballast water in untreated tanks on the carrier had a bacterial count of approximately $5 \times 10^3$ per ml, and sea water had a count of approximately $0.5 \times 10^3$ per ml.

When the test was started, a thick layer of oil could be seen floating on the surface of the solutions in Tanks A and B. The amount of oil present was estimated to be in the range of 2–5%. The oil layer in Tank B did not change in appearance throughout the run. The oil in Tank A, however, started to coagulate at about the 96th hour and streaks could be seen on the solution surface. The oil became "mushy" with the consistency of pudding at about the 100th hour, and as the test proceeded, more and more of the oil dispersed into the water phase.

At the 156th hour of the test, the solution in Tank A was discharged into the sea, and no oily material could be seen in the wake of the carrier. In contrast, when Tank B was discharged in a similar manner, a thick black expelled mixture was immediately observed, followed by a yellow oil slick in the wake of the carrier. Both tanks were then vented and washed for a few minutes with sea water using a hose at low pressure. In contrast to the normal oily appearance of emptied tanks, Tank A was relatively clean; there was no crude oil sludge and only small amounts of oil visible where the aerated culture solution reacted on the tank walls. It was evident that the tank could be used for clean ballast with only a low pressure water rinse. Tank B exhibited oil sludge throughout the compartment.

From the foregoing examples, it will be seen that the oil in the sea water was converted to a non-oily form both by means of the pure culture of RAG-1, as well as by cell-free solutions from RAG-1.

RAG-1 has the following characteristics:

During the exponential growth phase the cells appear mostly as irregular short rods, 0.9 to 1.2 by 1.5 to 3.0 $\mu$m. The cells occur often as V-shaped pairs, indicating snapping division. Occasionally the rods are slightly bent or swollen. Coccoid cells, approximately 1.2 μm in diameter, are characteristic of stationary phase cultures. The cocci are gram-positive; the rods are gram-negative.

Agar colonies: circular, glistening and smooth, up to 5.0 mm in diameter, gelatin is liquefied; starch is not hydrolyzed; indole and $H_2O_2$ are not produced; nitrites are produced from nitrate only when the cells are grown in citrate medium containing $KNO_3$; urease is not produced; catalase - positive; aerobic; hemolysis of rabbit blood agar; citrate can serve as the sole carbon and energy source; no acid from glucose, cellulose, maltose, lactose, rhamnose, sucrose or mannitol; optimum temperature 30° to 35°C. These properties characterize RAG-1 as a member of the genus Arthrobacter.

The invention is hereby claimed as follows:

1. A process for removing oil from sea water in ship compartments which comprises adding to oil-containing sea water in a ship compartment a microbial organism, a source of nitrogen and a source of phosphorus and converting the resultant mixture to a non-oily form with said microbial organism or the products of said microbial organism under aerobic conditions in said ship compartment, said microbial organism being the microbial organism herein defined at RAG-1.

2. A process as claimed in claim 1 wherein the conversion is effected with a cell-free solution which is a product of said microbial organism.

3. A process as claimed in claim 1 wherein aeration is effected by bubbling through a stream of air.

4. A process as claimed in claim 1 wherein the source of nitrogen is urea, ammonia, a nitrate or an ammonium salt.

5. A process as claimed in claim 1 wherein the source of phosphorus is a water soluble inorganic phosphate.

6. A process as claimed in claim 1 wherein by products are recovered from the resultant converted mixture.

* * * * *

UNITED STATES PATENT AND TRADEMARK OFFICE
CERTIFICATE OF CORRECTION

PATENT NO. : 3,941,692

DATED : March 2, 1976

INVENTOR(S) : DAVID GUTNICK and EUGENE ROSENBERG

It is certified that error appears in the above-identified patent and that said Letters Patent are hereby corrected as shown below:

Column 10, line 6, after "defined", "at" should read --as--.

Signed and Sealed this

Twentieth Day of July 1976

[SEAL]

Attest:

RUTH C. MASON
*Attesting Officer*

C. MARSHALL DANN
*Commissioner of Patents and Trademarks*